(12) United States Patent
Hansen et al.

(10) Patent No.: US 11,938,045 B2
(45) Date of Patent: Mar. 26, 2024

(54) BREATHABLE RESIDUAL-LIMB SOCKET SYSTEM
(71) Applicants: United States Government as Represented by the Department of Veterans Affairs, Washington, DC (US); Fraunhofer Gesellschaft zur Foerderung der angewandten Forschung e. V., Munich (DE)
(72) Inventors: Andrew Hansen, Minneapolis, MN (US); Sara Koehler-Mcnicholas, Minneapolis, MN (US); Eric Nickel, Minneapolis, MN (US); Kyle Barrons, Minneapolis, MN (US); Felix Starker, Munich (DE); Spencer Mion, Minneapolis, MN (US); John Ferguson, Minneapolis, MN (US); Stuart Fairhurst, Minneapolis, MN (US); Ellankavi Ramasamy, Munich (DE); Karl Koester, Minneapolis, MN (US); Urs Schneider, Munich (DE)
(73) Assignees: United States Government As Represented By The Department Of Veterans Affairs, Washington, DC (US); Fraunhofer-Gesellschaft zur Foerderung der angewandten Forschung e. V., Munich (DE)
( * ) Notice: Subject to any disclaimer, the term of this patent is extended or adjusted under 35 U.S.C. 154(b) by 0 days.
(21) Appl. No.: 17/993,303
(22) Filed: Nov. 23, 2022
(65) Prior Publication Data
US 2023/0157851 A1 May 25, 2023

Related U.S. Application Data

(63) Continuation of application No. 16/629,822, filed as application No. PCT/US2018/041519 on Jul. 10, 2018, now abandoned.
(60) Provisional application No. 62/530,762, filed on Jul. 10, 2017.

(51) Int. Cl.
A61F 2/78 (2006.01)
A61F 2/50 (2006.01)
A61F 2/80 (2006.01)
A61F 13/00 (2006.01)
(52) U.S. Cl.
CPC .......... *A61F 2/7812* (2013.01); *A61F 2/5044* (2013.01); *A61F 2/80* (2013.01); *A61F 2002/5055* (2013.01); *A61F 2002/7818* (2013.01); *A61F 2002/785* (2013.01);
(Continued)
(58) Field of Classification Search
CPC ................................. A61F 2/7812–2002/785
See application file for complete search history.

*Primary Examiner* — David H Willse
(74) *Attorney, Agent, or Firm* — Ballard Spahr LLP

(57) ABSTRACT

Breathable residual-limb system that admits air and allows sweat to evaporate from the surface of the residual limb. In an embodiment, the system comprises a liner sock to be worn on the residual limb, and comprising air-permeable textile forming a substantially cylindrical portion that is closed on a distal end and open on a proximal end and comprising an internal surface and an external surface. The liner sock further comprises a friction-interface material that covers only a portion of the internal surface of the air-permeable textile, such that, when worn on the residual limb, the friction-interface material contacts a surface of the residual limb, and an uncovered portion of the air-permeable textile which the friction-interface material does not cover allows air to pass between an external environment of the liner sock and the surface of the residual limb.

18 Claims, 15 Drawing Sheets

(52) U.S. Cl.
CPC ............... *A61F 2002/7875* (2013.01); *A61F 2013/00097* (2013.01); *A61F 2013/00136* (2013.01)

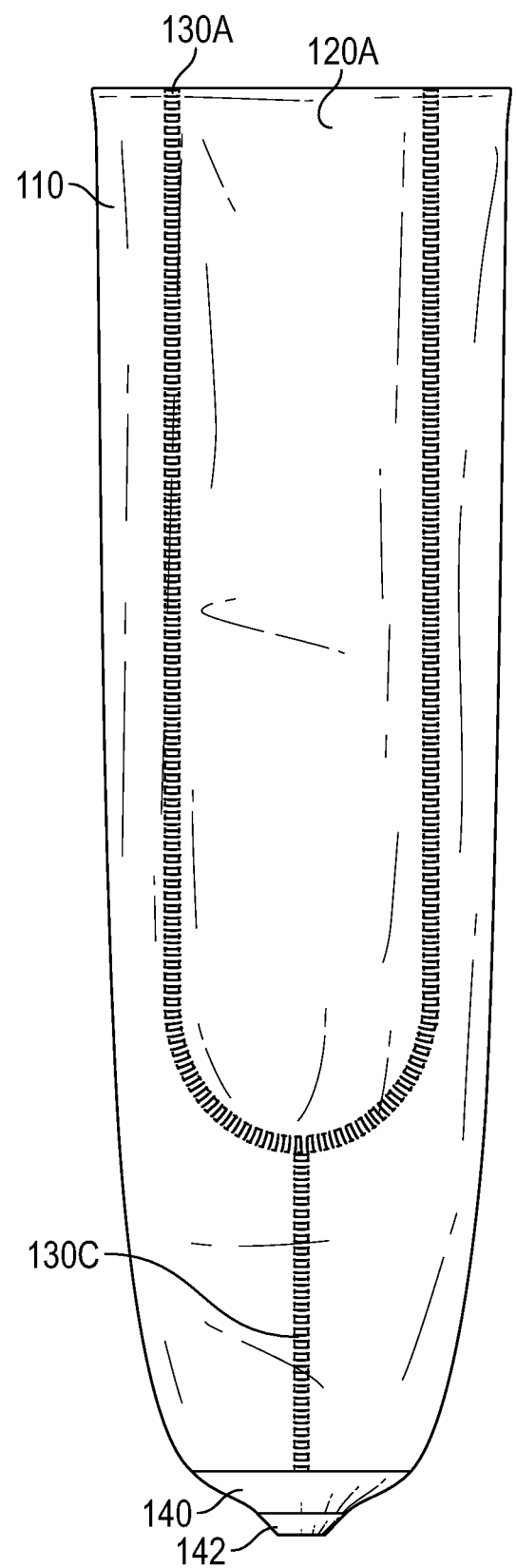
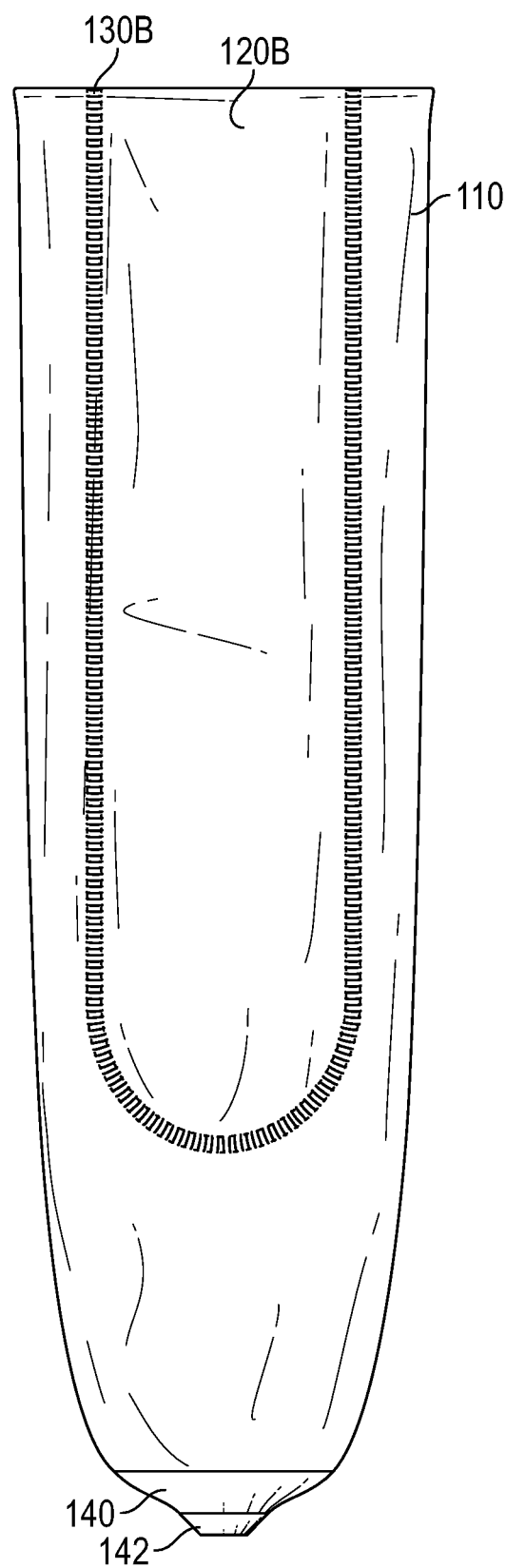
FIG. 2A  FIG. 2B

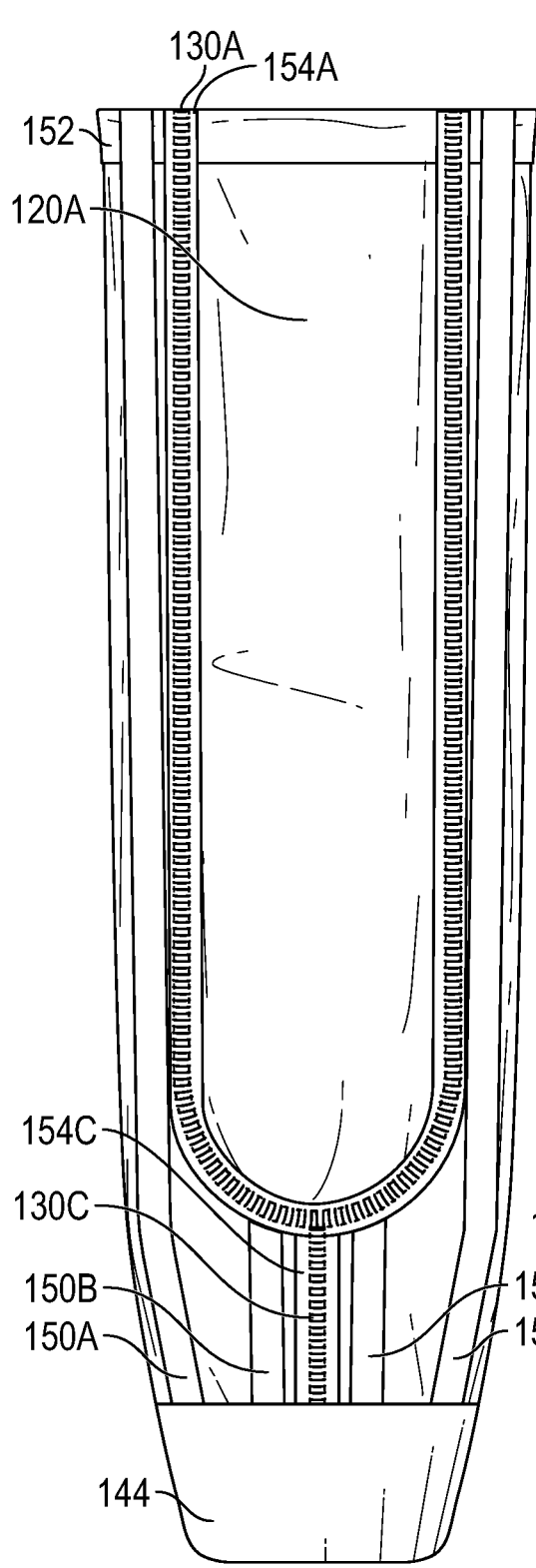 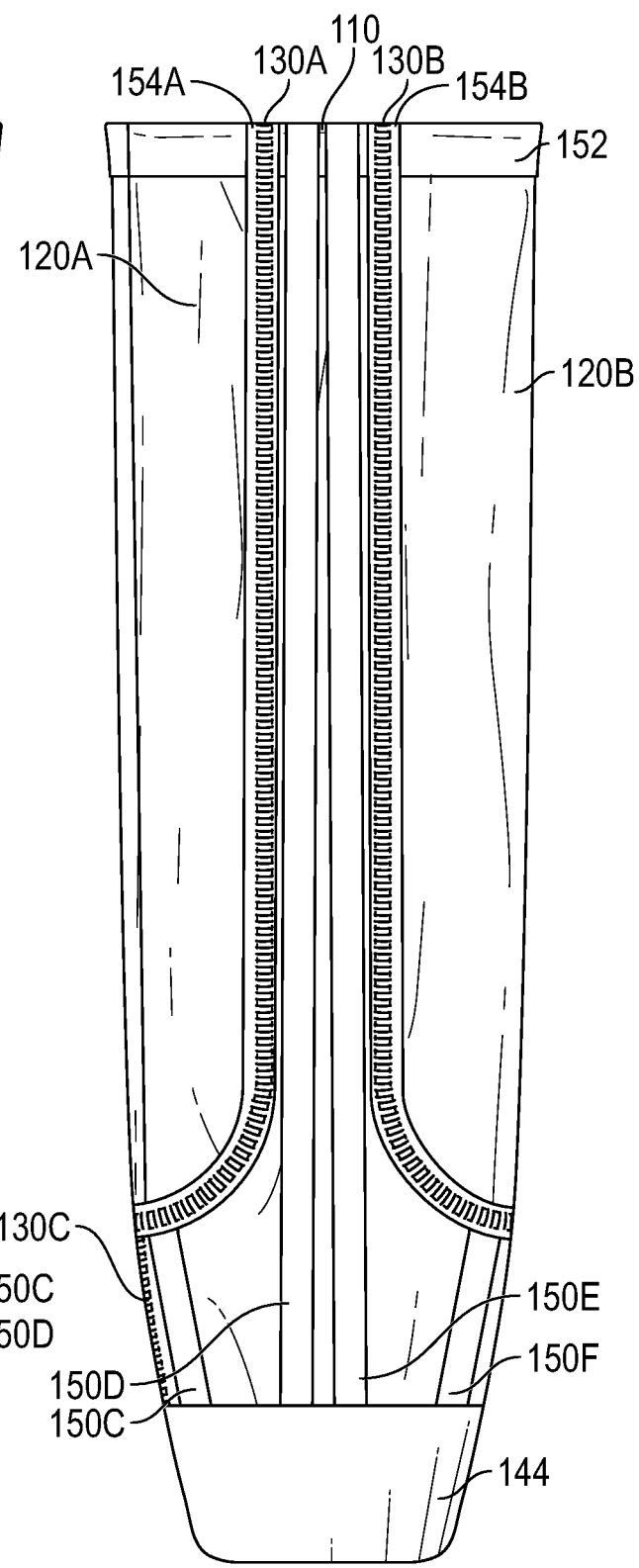
FIG. 3A  FIG. 3B

BREATHABLE RESIDUAL-LIMB SOCKET SYSTEM

CROSS-REFERENCE TO RELATED APPLICATIONS

This application is a continuation of U.S. patent application Ser. No. 16/629,822, filed on Jan. 9, 2020, now abandoned, which is a U.S. national phase under § 371 of International Patent Application No. PCT/US18/41519, filed on Jul. 10, 2018, which claims priority to U.S. Provisional Patent Application No. 62/530,762, filed on Jul. 10, 2017. The entirety of each of these applications is hereby incorporated herein by reference.

GOVERNMENT LICENSE RIGHTS

This invention was made with government support under Contract No. W81XWH-14-2-0197, awarded by the Department of Defense. The government may have certain rights in the invention.

BACKGROUND

Field of the Invention

The embodiments described herein are generally directed to a residual limb socket system, and, more particularly, to a breathable residual-limb socket system that admits air and allows sweat to evaporate from the surface of the residual limb.

Description of the Related Art

Conventional residual-limb socket systems utilize a liner, which is pulled over the residual limb, in conjunction with a socket, which is pulled over the liner. However, these conventional prostheses often use materials that have thermally insulating properties. For example, conventional liners are made of thick rubber, foam, or leather. This creates a microclimate in which heat, trapped inside the socket, can make the residual limb hot, sweaty, and uncomfortable. These hot, moist conditions within the prostheses can exacerbate skin problems on the residual limb, as well as reduce mobility and function of the residual limb.

Some liners, such as the Endolite Silcare Breathe™ and Uniprox SoftSkin Air™, have micro-pores to improve breathability. However, as confirmed by testing, even with these micro-pores in the liner, the residual limb is not able to receive the amount of air necessary for evaporative cooling.

Thus, what is needed is a breathable residual-limb socket system that is sufficiently air-permeable so as to allow evaporative cooling on the surface of the residual limb.

SUMMARY

Accordingly, a breathable residual-limb socket system is disclosed. In an embodiment, the system comprises a liner sock to be worn on the residual limb, the liner sock comprising: air-permeable textile forming a substantially cylindrical portion that is closed on a distal end and open on a proximal end and comprising an internal surface and an external surface; and a friction-interface material that covers only a portion of the internal surface of the air-permeable textile, such that, when worn on the residual limb, the friction-interface material contacts a surface of the residual limb, and an uncovered portion of the air-permeable textile which the friction-interface material does not cover allows air to pass between an external environment of the liner sock and the surface of the residual limb.

In an embodiment, the air-permeable textile comprises: a first section comprising unidirectional-stretch textile; and at least one second section comprising bidirectional-stretch textile. The first section may be fixed to the at least one second section by at least one seam, and the friction-interface material may cover the seam on the internal surface of the air-permeable textile. The air-permeable textile may comprise two second sections comprising bidirectional-stretch textile. The friction-interface material may cover an entire internal surface of the first section comprising unidirectional-stretch textile, but not cover an entire internal surface of the at least one section comprising bidirectional-stretch textile.

In an embodiment, the friction-interface material comprises a plurality of longitudinal strips that extend in a longitudinal direction of the liner sock and that are spaced apart from each adjacent one of the plurality of longitudinal strips, around a circumference of the liner sock, by the uncovered portion of the air-permeable textile. The friction-interface material may comprise a strip that extends around a circumference of the liner sock at a proximal end of the liner sock. The friction-interface material may comprise a plurality of circumferential strips that extend around a circumference of the liner sock and that are spaced apart from each adjacent one of the plurality of circumferential strips, in a longitudinal direction of the liner sock, by the uncovered portion of the air-permeable textile. In an embodiment, the friction-interface material comprises a plurality of dots. The friction-interface material may comprise a distal cup at a distal end of the liner sock. The friction-interface material may comprise silicone gel.

In an embodiment, the liner sock further comprises a distal cap on an external surface of the closed distal end of the liner sock. The distal cap may comprise a countersunk threaded hole configured to receive a screw pin.

In an embodiment, the system further comprises a socket to be worn, either directly or indirectly, over the liner sock, the socket comprising: a perforated inner layer; and an outer frame comprising one or more fenestrations, through which the perforated inner layer is exposed to an external environment of the socket. The perforated inner layer may comprise a plurality of holes having a diameter of 5 millimeters or less. The outer frame may comprise an anterior fenestration and at least one posterior fenestration. The outer frame may comprise at least two posterior fenestrations. The perforated inner layer may comprise fabric. The outer frame may comprise carbon fiber.

BRIEF DESCRIPTION OF THE DRAWINGS

The details of the present invention, both as to its structure and operation, may be gleaned in part by study of the accompanying drawings, in which like reference numerals refer to like parts, and in which:

FIGS. 2A-2C illustrate exterior plan views of a liner sock, according to an embodiment;

FIGS. 3A and 3B illustrate interior plan views of a liner sock, according to a first embodiment;

DETAILED DESCRIPTION

In an embodiment, a breathable residual-limb socket system is disclosed. After reading this description, it will become apparent to one skilled in the art how to implement the invention in various alternative embodiments and alternative applications. However, although various embodiments of the present invention will be described herein, it is understood that these embodiments are presented by way of example and illustration only, and not limitation. As such, this detailed description of various embodiments should not be construed to limit the scope or breadth of the present invention as set forth in the appended claims.

1. System

In an embodiment, the breathable residual-limb socket system comprises one or both of a liner sock and a socket.

1.1. Liner Sock

Figure 1A:
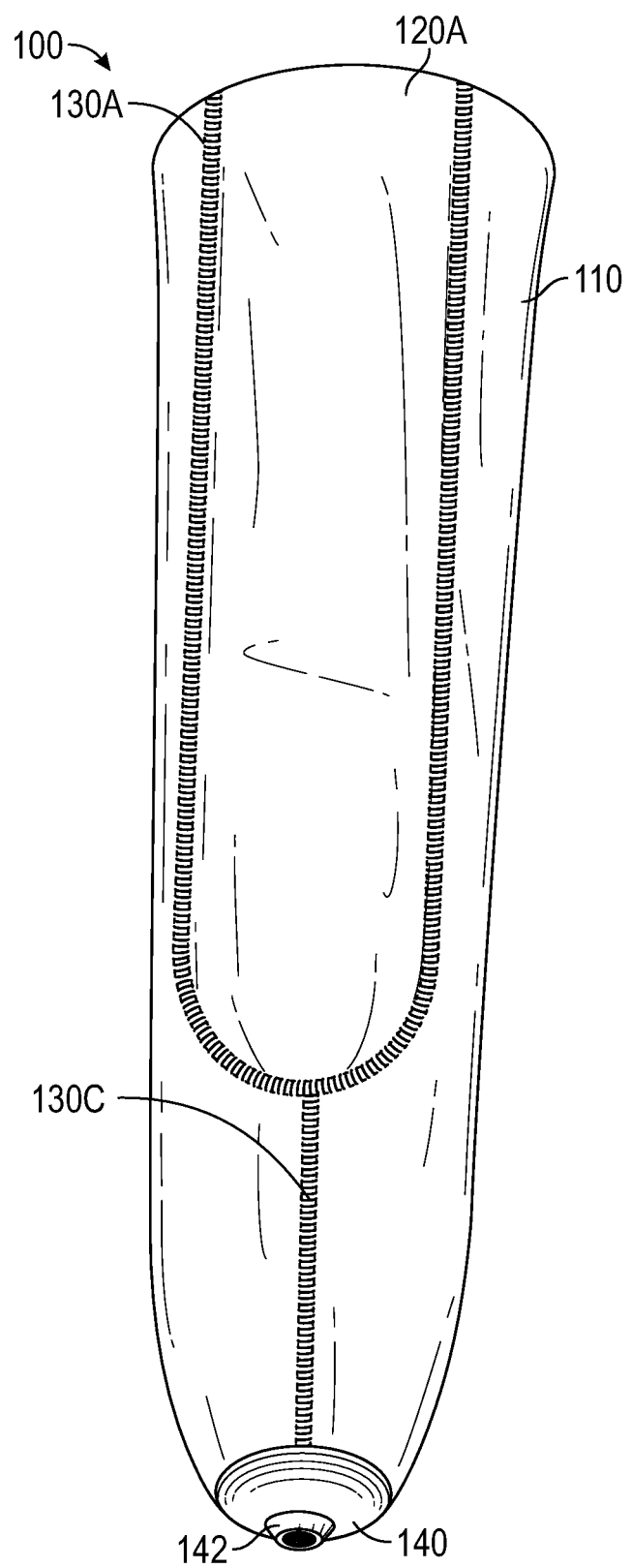
FIGS. 1A-1C illustrate exterior perspective views of a liner sock, according to an embodiment.
Figure 1B:
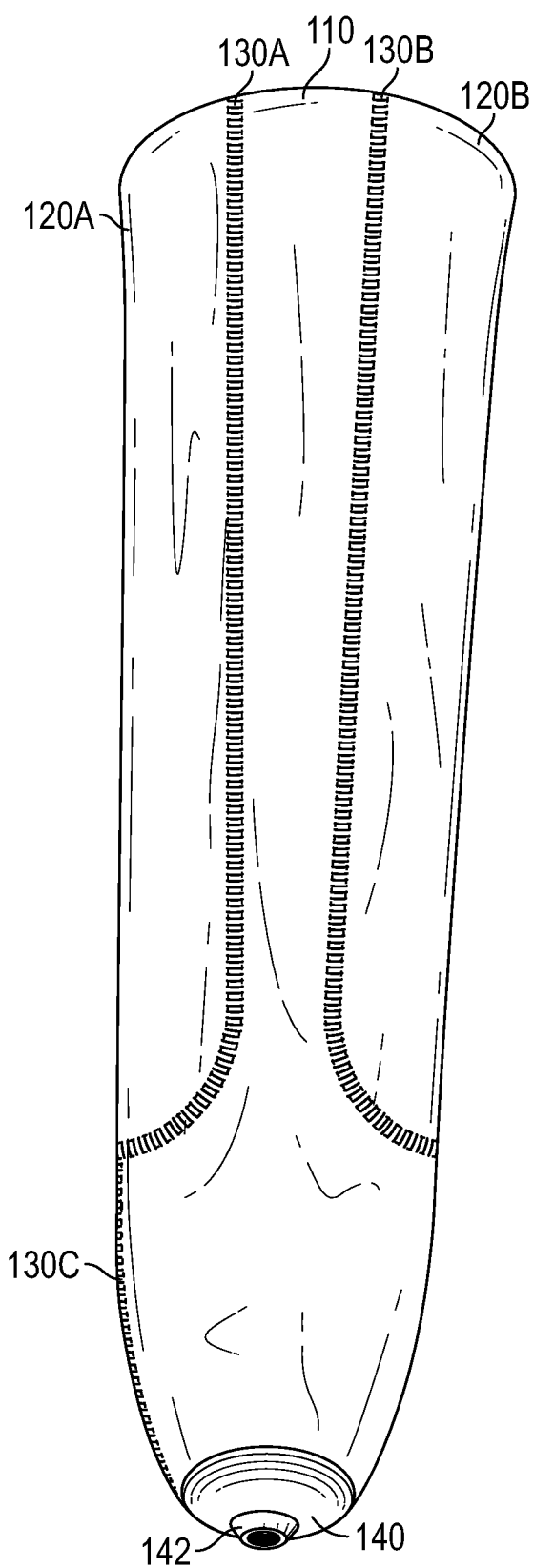

FIG. 1A illustrates a perspective view, from a distal end to a proximal end, of the front of the exterior of a liner sock 100, while FIG. 1B illustrates a side of the exterior of liner sock 100 (e.g., the liner sock 100 in FIG. 1A, rotated 90° to the left), according to an embodiment. Liner sock 100 may be formed from at least one section 110 of unidirectional-stretch textile and at least one section 120 of bidirectional-stretch textile. The unidirectional-stretch textile of section(s) 110 is manufactured to have elasticity primarily in a single direction (e.g., in the longitudinal direction of liner sock 100), whereas the bidirectional-stretch textile of section(s) 120 is manufactured to have elasticity primarily in two directions (e.g., in the longitudinal and lateral directions of liner sock 100). The unidirectional-stretch textile and/or the bidirectional-stretch textile should be air-permeable and/or breathable, so as to allow evaporative cooling through the textile.

In the illustrated embodiment, liner sock 100 comprises a single section 110 of unidirectional-stretch textile and two sections 120A and 120B of bidirectional-stretch textile. As shown sections 120A and 120B of bidirectional-stretch textile are each generally rectangular with a curved distal end. Each section 120A and 120B of bidirectional-stretch textile is joined to section 110 of unidirectional-stretch textile by a U-shaped seam 130A and 130B, respectively. In addition, opposing edges of section 110 of unidirectional-stretch textile may be joined to each other by seam 130C, to form a substantially cylindrical or partially cylindrical liner sock 100. Bidirectional-stretch sections 120A and 120B may be on opposite sides of the substantially cylindrical portion of liner sock 100, such that, around a circumference of liner sock 100, bidirectional-stretch sections 120A and 120B are spaced apart from each other on both sides by interposed portions of unidirectional-stretch section 110.

In an embodiment, the distal end of liner sock 100 comprises a distal cap 140 and a threaded countersunk hole 142 for receiving a screw pin 146. Distal cap 140 is affixed to the distal end of unidirectional-stretch section 100 and/or an internal distal cup (e.g., distal cup 144, illustrated in other figures), with a distal portion of unidirectional-stretch section 110 sandwiched between distal cap 140 and the distal cup, to thereby close the distal end of liner sock 100. Distal cap may comprise or consist of polyurethane rubber or a similar material, and may be affixed to liner sock 100 and/or the distal cup within liner sock 100 via stitching, adhesives, and/or the like. Countersunk hole 142 is configured to receive a standard, threaded screw pin 146, which is commonly used for the suspension of prosthetic limbs. Of course, the proximal end of liner sock 100 remains open or openable to receive the residual limb of the user.

Figure 1C:
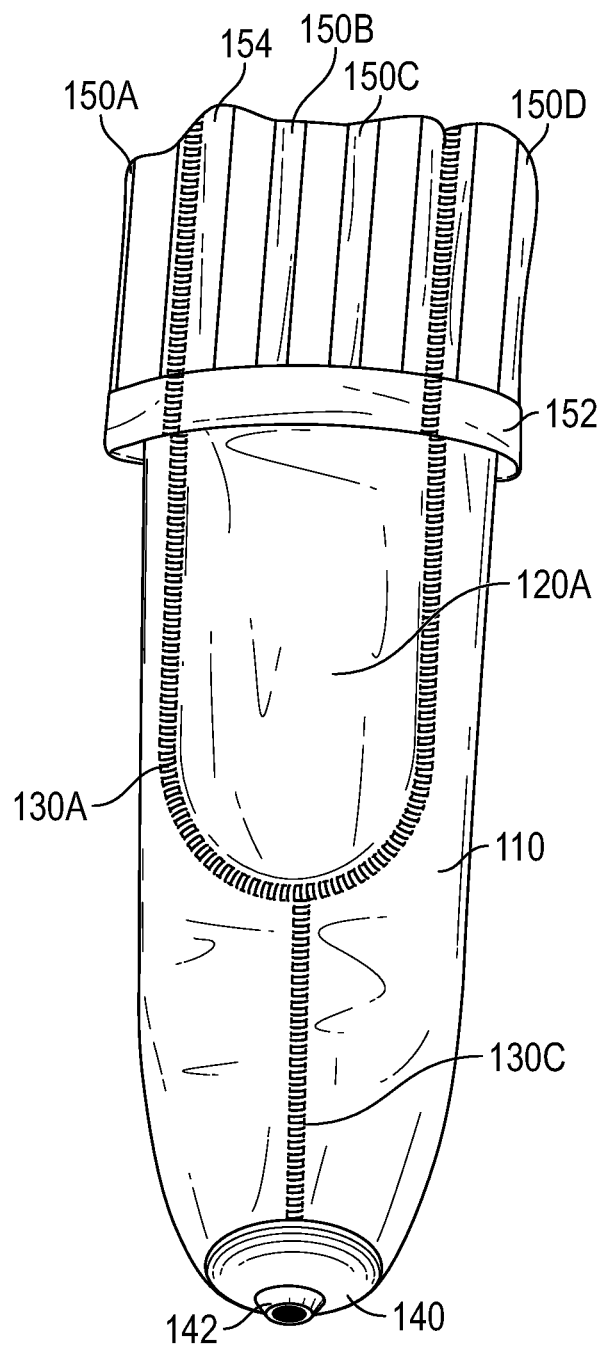

FIG. 1C illustrates the front of liner sock 100, with the proximal end of liner sock 100 partially rolled down to show an interior portion of liner sock 100, according to an embodiment. As shown, the internal surface of liner sock 100 may comprise strips 150, 152, and/or 154. Each strip 150, 152, and/or 154 may comprise or consist of silicone gel or a similar friction-interface material.

In an embodiment, a plurality of spaced longitudinal strips 150 extend longitudinally (i.e., vertically when liner sock is upright) down the internal surface of liner sock 100. A circumferential strip 152 may also be provided around the entire circumference of liner sock 100 at or near the proximal end of liner sock 100. In addition, a plurality of seam strips 154 may cover the internal surface of seams 130, to prevent liner sock 100 from slipping, as well as to prevent seams 130 from irritating the skin of the residual limb. It should be understood that the internal surfaces of seams 130A, 130B, and 130C may each be covered by a seam strip 154, and that the respective seam strip 154 may follow the curvature of seams 130A and 130B.

Strips 150, 152, and/or 154 may be sized and spaced to provide a comfortable friction fit, while allowing a significant portion of the internal surface of liner sock 100 (e.g., 50% or more of the internal surface) to remain uncovered. In addition, strips 150, 152, and/or 154 may be positioned over targeted anatomical regions to provide cushioning to sensitive anatomical regions (e.g., the distal tibia, tibial tubercle, tibial crest, tibial condyles, fibular head, etc.) and/or suspension loading to tolerant anatomical regions (e.g., patellar tendon, medial tibial flare, fibular shaft, popliteal fossa, gastrocnemius, etc.). The friction fit, provided by strips 150, 152, and/or 154, prevents liner sock 100 from slipping off of the residual limb during use of a suspended prosthesis, while the uncovered portions of the internal surface of liner sock 100 (i.e., in conjunction with the uncovered external surface of liner sock 100) allow air to permeate the textile of liner sock 100. This air-permeability of liner sock 100 enables evaporative cooling on the skin of the residual limb within liner sock 100.

Figure 2C:
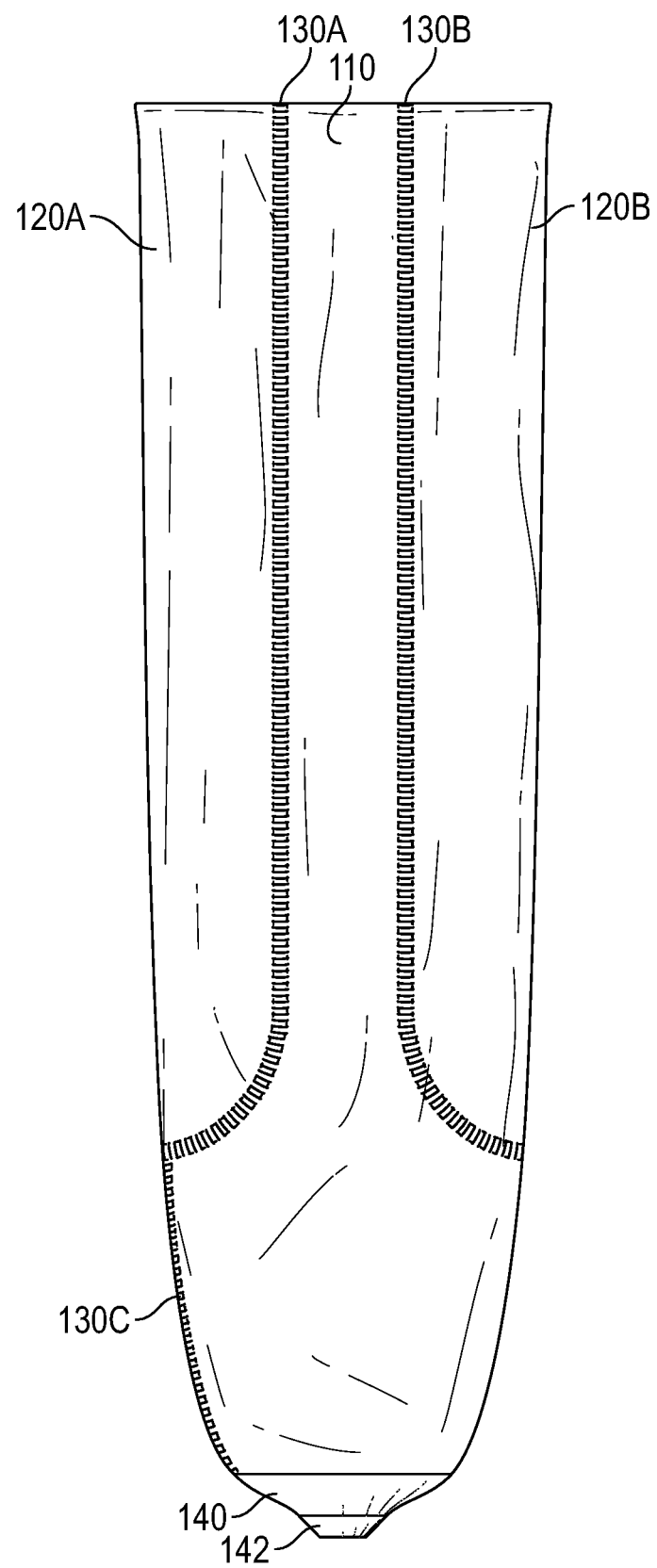

FIG. 2A-2C illustrate plan views of liner sock 100, according to an embodiment. Specifically, FIG. 2A illustrates a front view of liner sock 100, FIG. 2B illustrates a back view of liner sock 100, and FIG. 2C illustrates a side view of liner sock 100. It should be understood that, with respect to liner sock 100, the terms "front," "side," and back" are simply used for the convenience of relating the illustrations to each other, and that liner sock 100 does not need to be oriented on the residual limb in any particular fashion (e.g., the front of liner sock 100 may be aligned to the posterior of the residual limb, etc.). However, to obtain the benefit of sections 120A and 120B of bidirectional-stretch textile, one of these sections 120A and 120B should be oriented on the anterior of the residual limb (e.g., such that it passes over the front of the knee), while the other one of these sections should be oriented on the posterior of the residual limb (e.g., such that it passes over the back of the knee).

FIGS. 3A and 3B illustrate front and side views of an internal surface of liner sock 100, according to a first embodiment. In other words, these views illustrate liner sock 100 when flipped inside-out. As shown, the internal surface of liner sock 100 comprises strips 150, 152, and 154, which may comprise or consist of silicone gel or a similar friction-interface material, as is commonly used for cushioning residual-limb liners and is well known in the art. Longitudinal strips 150 comprise N strips extending longitudinally across a portion or an entirety of the longitudinal length of the inner surface of liner sock 100. N may be any number greater than or equal to one and preferably greater than one. However, as discussed elsewhere herein, longitudinal strips 150 should be numbered and spaced so as to leave uncovered textile between adjacent pairs of longitudinal strips 150. For example, each longitudinal strip 150 may be approximately half-an-inch in width and be spaced from each adjacent longitudinal strip 150, along the circumference of liner sock 100, by approximately half-an-inch or more.

While longitudinal strips 150 are shown as stopping at seams 130A and 130B and not extending across sections 120A and 120B of bidirectional-stretch textile, in alternative embodiments, strips 150 may extend longitudinally across sections 120A and 120B (e.g., as demonstrated in FIG. 1C). Circumferential strip 152 is a continuous strip along the entire circumference of a proximal end of the internal surface of liner sock 100. Strips 154 cover and follow the inner surfaces of seams 130, to prevent or reduce contact between seams 130 and the skin of the user's residual limb, thereby preventing or reducing skin irritation.

In an embodiment, the internal surface of liner sock 100 comprises a distal cup 144. Distal cup 144 may comprise silicone gel or a similar friction-interface material, and may comprise the same material or a different material than strips 150, 152, and/or 154. In an embodiment, distal cup 144 comprises the same material as strips 150, 152, and/or 154, but has greater thickness. Distal cup 144 is configured to comfortably receive the distal end of the user's residual limb. Preferably, distal cup 144 should have a low durometric measure to aid in comfort at the distal end of the residual limb.

Figure 4A:
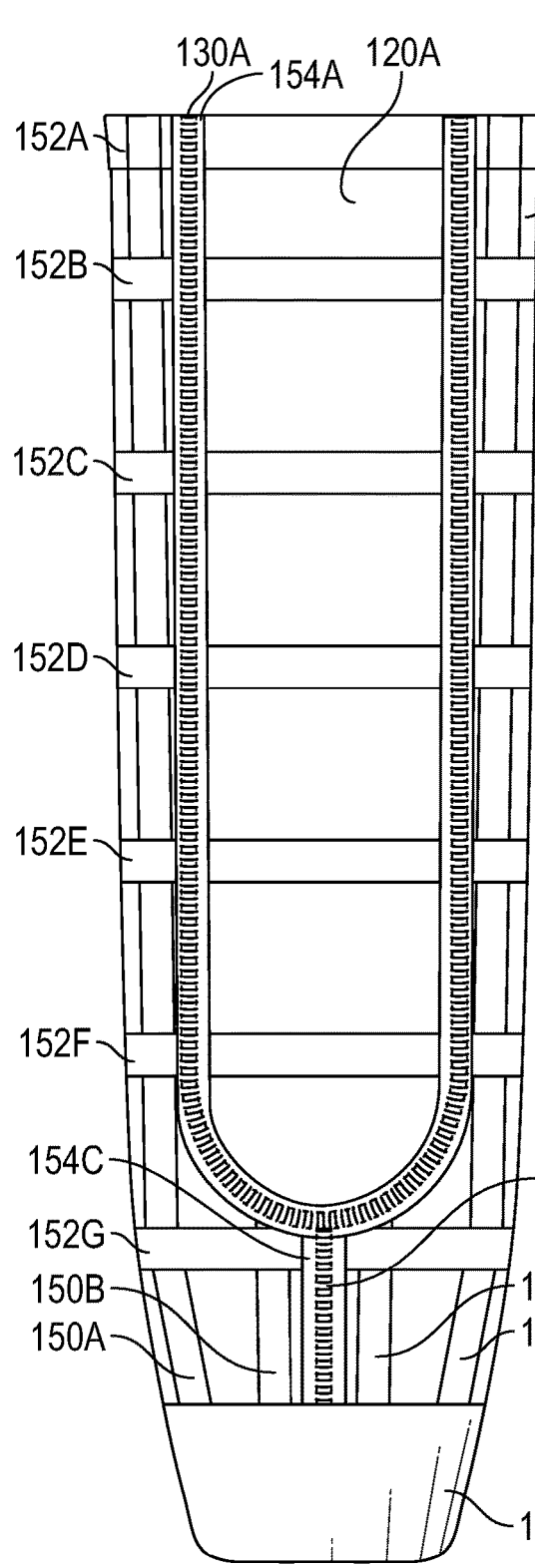
FIGS. 4A and 4B illustrate interior plan views of a liner sock, according to a second embodiment.
Figure 4B:
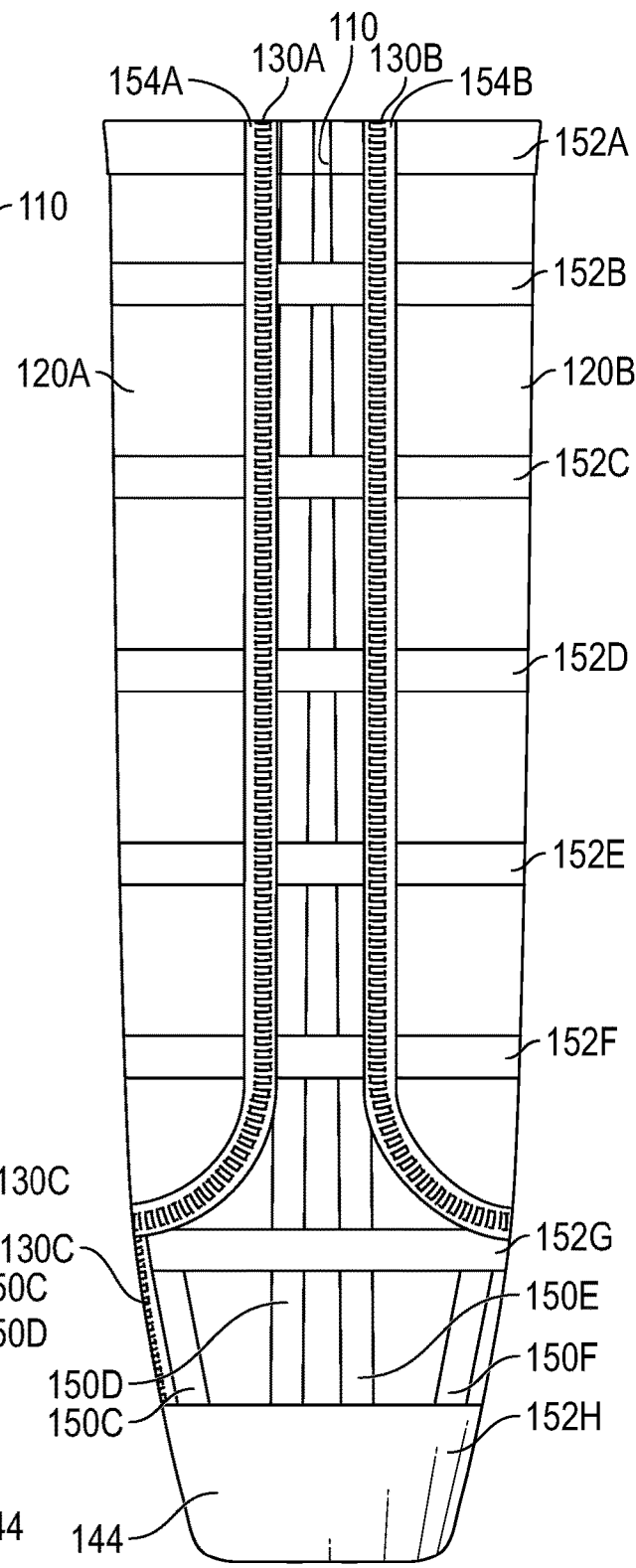

FIGS. 4A and 4B illustrate front and side views of an internal surface of liner sock 100, according to an alternative, second embodiment. In this second embodiment, longitudinal strips 150 and seams strips 154 may be the same as described above. However, in this second embodiment the internal surface of liner sock 100 comprises a plurality of circumferential strips 152, with each circumferential strip 152 extending along the entire circumference of liner sock 100. The number of circumferential strips 152 may comprise any number greater than one. However, as discussed elsewhere herein, circumferential strips 152 should be numbered and spaced so as to leave uncovered textile between adjacent pairs of circumferential strips 152. For example, each circumferential strip 152 may be approximately half-an-inch in width and be spaced from each adjacent circumferential strip 152, along the longitudinal axis of liner sock 100, by approximately half-an-inch or more.

Circumferential strips 152 may be spaced substantially equidistantly along the longitudinal axis of liner sock 100. As shown, circumferential strips 152 extend across sections 120A and 120B of bidirectional-stretch textile. However, in alternative embodiments, at least some of circumferential strips 152 may extend circumferentially across section 110 of unidirectional-stretch textile, but stop at seams 130A and 130B so as not to extend circumferentially across sections 120A and 120B of bidirectional-stretch textile.

Figure 5A:
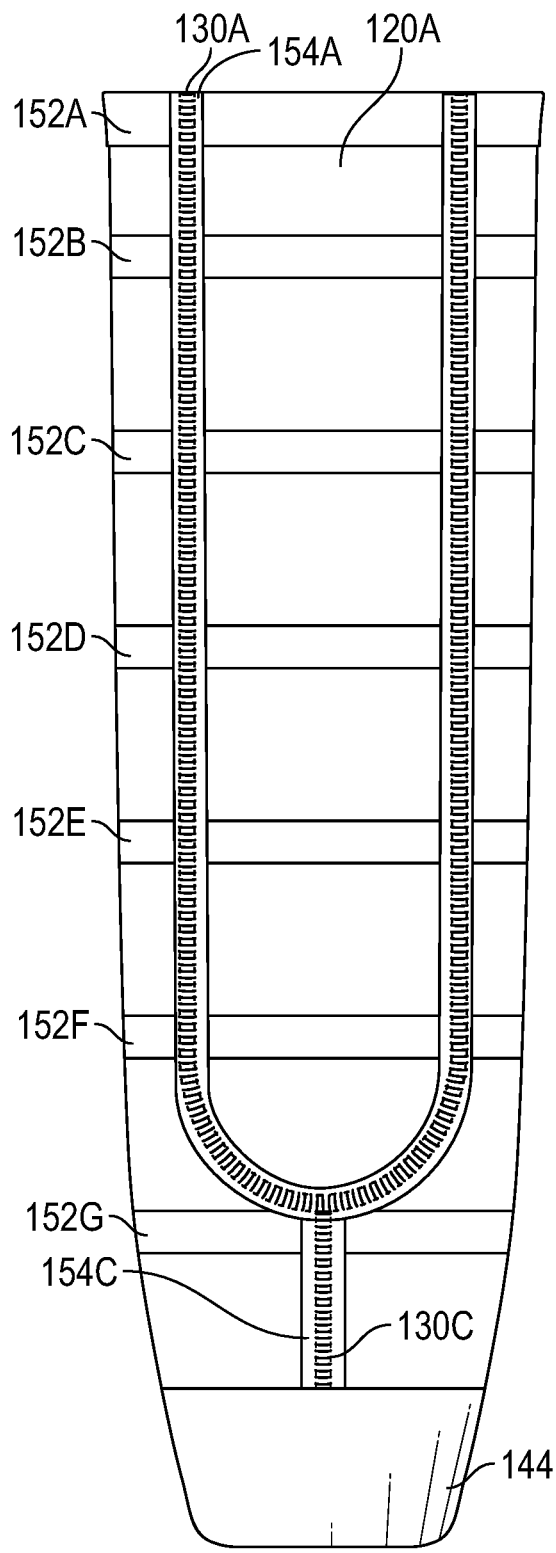
FIGS. 5A and 5B illustrate interior plan views of a liner sock, according to a third embodiment.
Figure 5B:
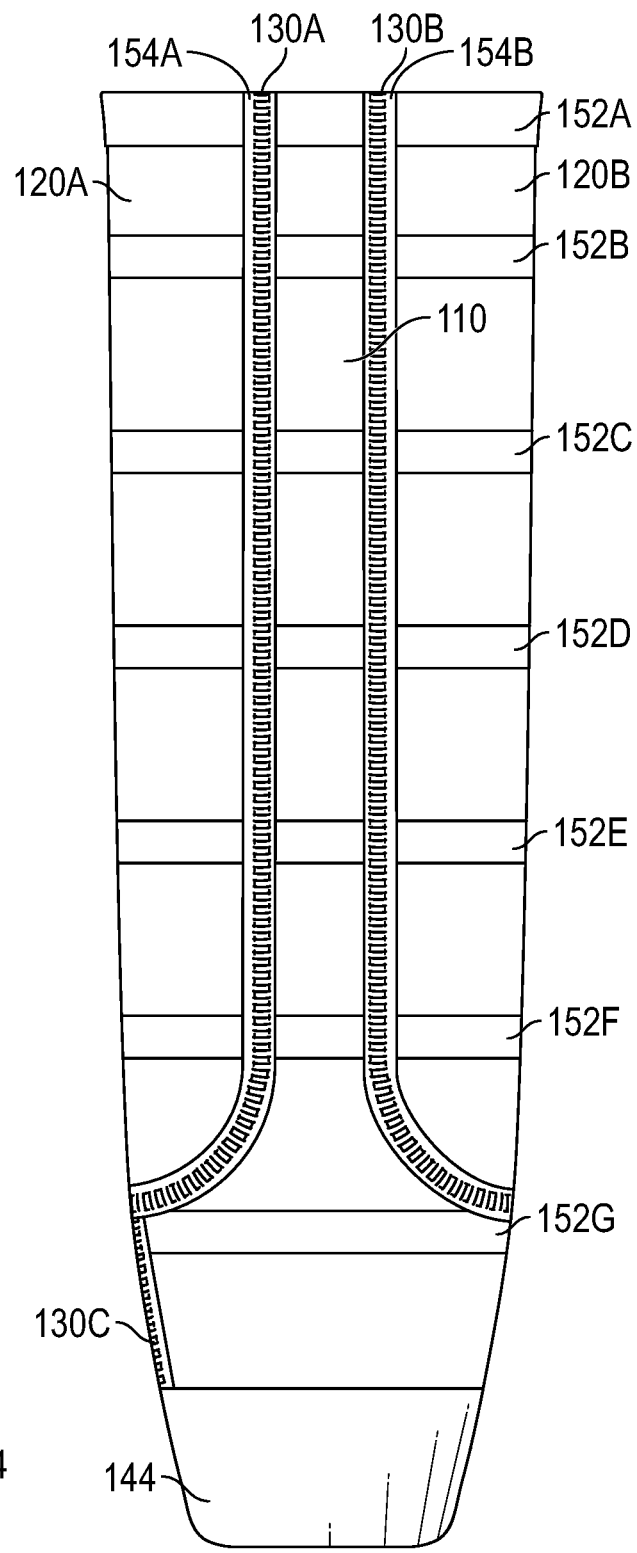

FIGS. 5A and 5B illustrate front and side views of an internal surface of liner sock 100, according to an alternative, third embodiment. In this third embodiment, seam strips 154 may be the same as described above, and the internal surface of liner sock 100 may comprise the same plurality of circumferential strips 152 described in the second embodiment illustrated in FIGS. 4A and 4B. However, in the third embodiment, the internal surface of liner sock 100 does not comprise any longitudinal strips 150.

Advantageously, in embodiments which utilize a plurality of spaced circumferential strips 152 (e.g., the second embodiment illustrated in FIGS. 4A and 4B, and the third embodiment illustrated in FIGS. 5A and 5B), liner sock 100 can be cut to size and still have a proximal circumferential strip 152. Specifically, to shorten liner sock 100 to more appropriately match the length of the residual limb, a user can cut liner sock 100 laterally. For example, if the user cuts liner sock 100 laterally between circumferential strips 152C and 152D, circumferential strips 152A, 152B, and 152C will be discarded with the separated portion of liner sock 100, and circumferential strip 152D will act as the new proximal circumferential strip to comfortably friction-fit the proximal edge of liner sock 100 to the residual limb.

Figure 6A:
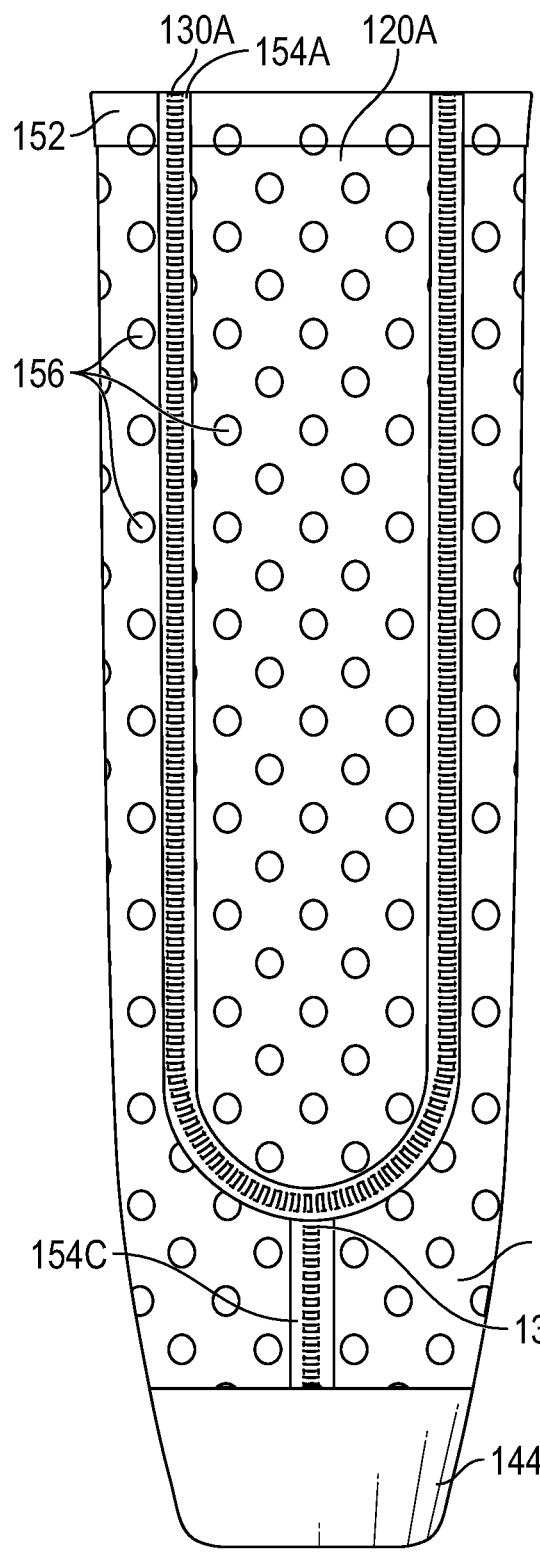
FIGS. 6A and 6B illustrate interior plan views of a liner sock, according to a fourth embodiment.
Figure 6B:
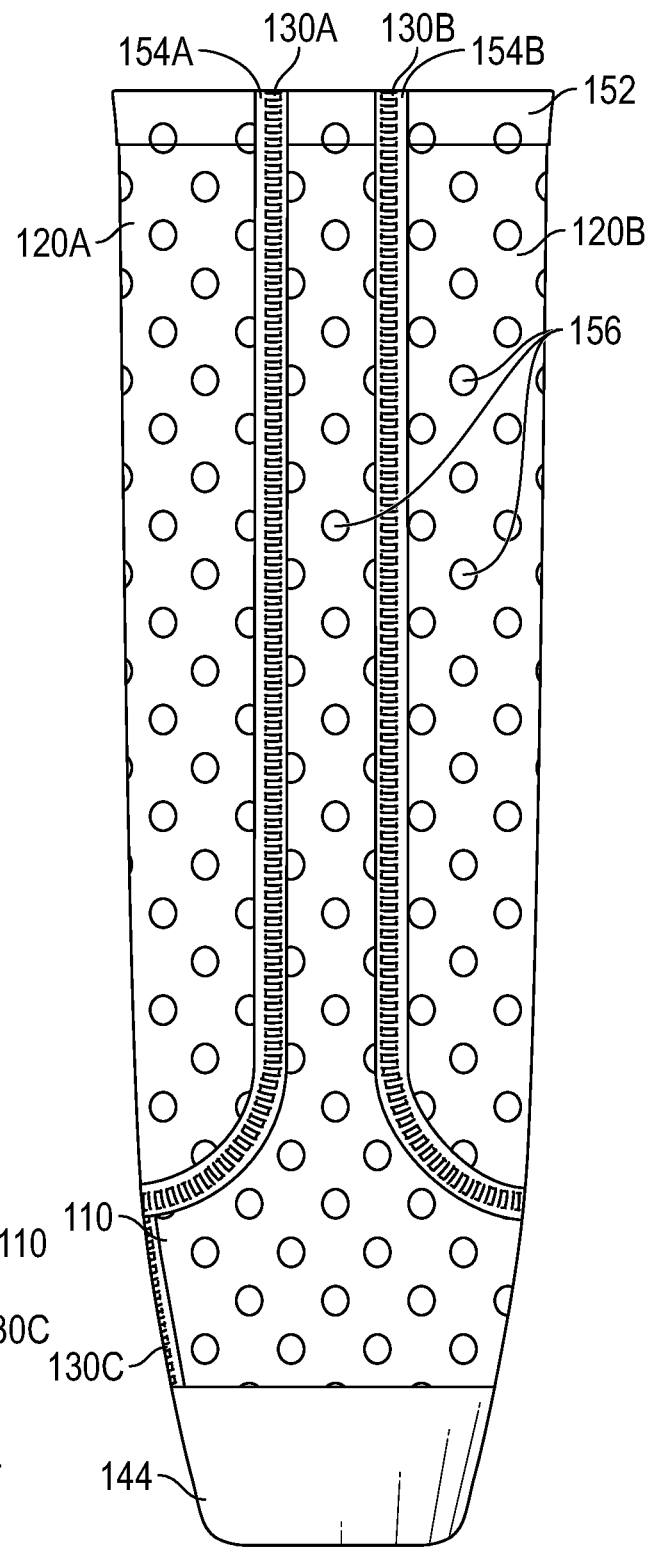

FIGS. 6A and 6B illustrate front and side views of an internal surface of liner sock 100, according to an alternative, fourth embodiment. In this fourth embodiment, the internal surface of liner sock 100 comprises dots 156. Like strips 150, 152, and/or 154, dots 156 may comprise or consist of silicone gel or a similar friction-interface material, and provide the same comfort, friction fit as strips 150, 152, and/or 154. The internal surface of liner sock 100 may still comprise circumferential strip 152 along the proximal, internal circumference of liner sock 100, and/or may still comprise seam strips 154 following the internal surfaces of seams 130. Alternatively, the internal surface of liner sock 100 may comprise only dots 156, i.e., without any of strips 150, 152, and 154.

Figures 7A, 7B:
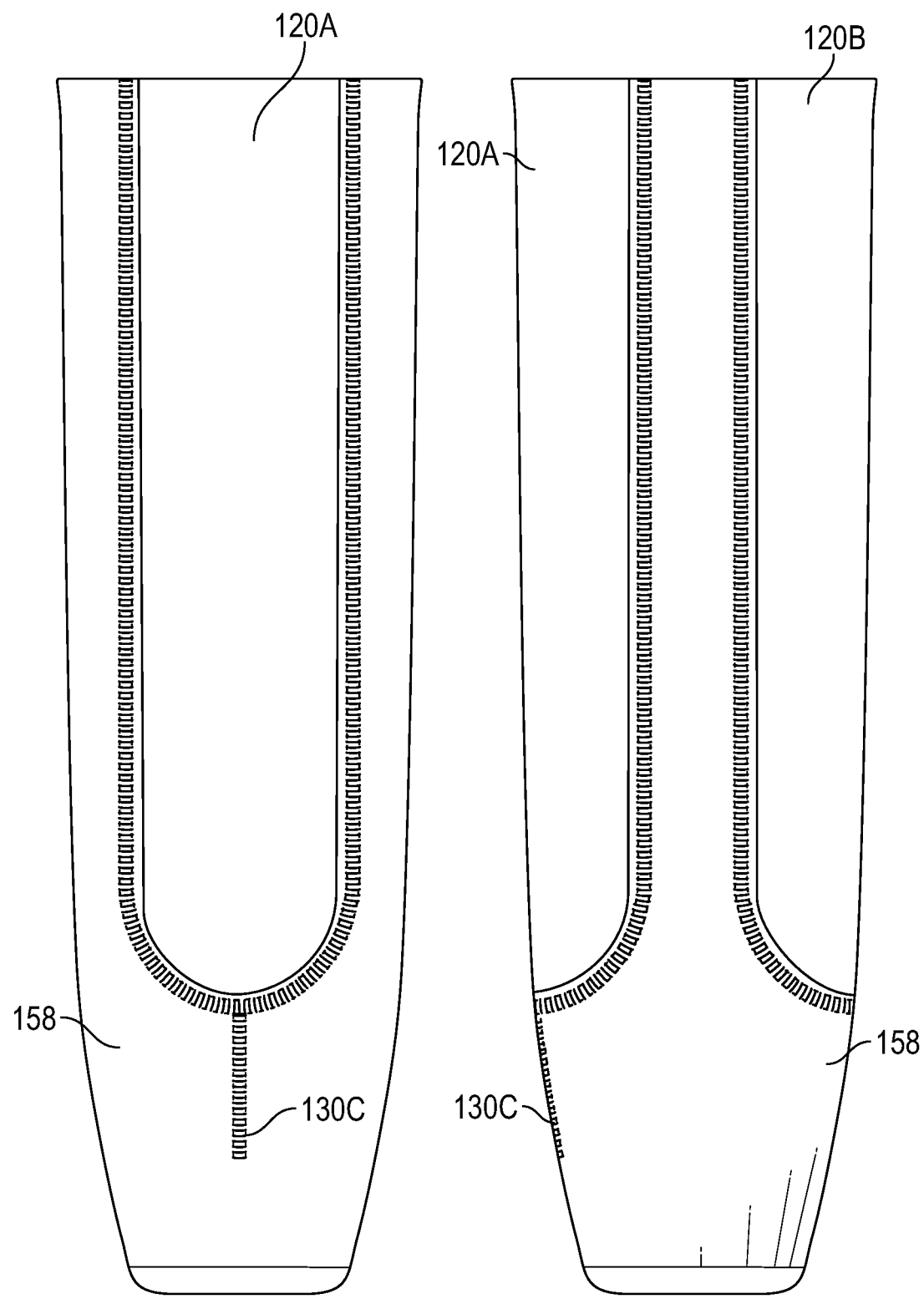
FIGS. 7A and 7B illustrate interior plan views of a liner sock, according to a fifth embodiment.

FIGS. 7A and 7B illustrate front and side views of an internal surface of liner sock 100, according to an alternative, fifth embodiment. In this fifth embodiment, the internal surface of section 110 of unidirectional-stretch textile of liner sock 100 is entirely covered by material 158, whereas the internal surfaces of sections 120A and 120B of bidirectional-stretch textile are not covered by any material (or only partially covered by material 158 within a vicinity of seams 130). Notably, the internal surfaces of seams 130 may be covered by material 158. Like strips 150, 152, and/or 154, and/or dots 156, material 158 may comprise or consist of silicone gel or a similar friction-interface material, and provide the same comfort, friction fit as strips 150, 152, and/or 154, and/or dots 156.

1.2. Socket

FIGS. 8A-8F illustrates a socket 200, according to a first embodiment. In the illustrated embodiment, socket 200 comprises a perforated inner layer 210 and an outer frame 220. Socket 200 may be worn over a stump sock 300, which is worn over liner sock 100. Stump sock 300 can be used to provide volume management. Specifically, the volume of the residual limb may change throughout the course of a day. Thus, stump socks 300 of differing thicknesses (i.e., different ply) may be used, throughout the day, to fill the varying amounts of space between liner sock 100 and socket 200, caused by the changes in limb volume. Stump sock 300 and socket 200 both comprise holes at their distal ends to allow the passage of a pin screw (e.g., pin screw 146 in FIGS. 10A-10C), when the pin screw is threaded into countersunk hole 142 of liner sock 100.

Figure 8A:
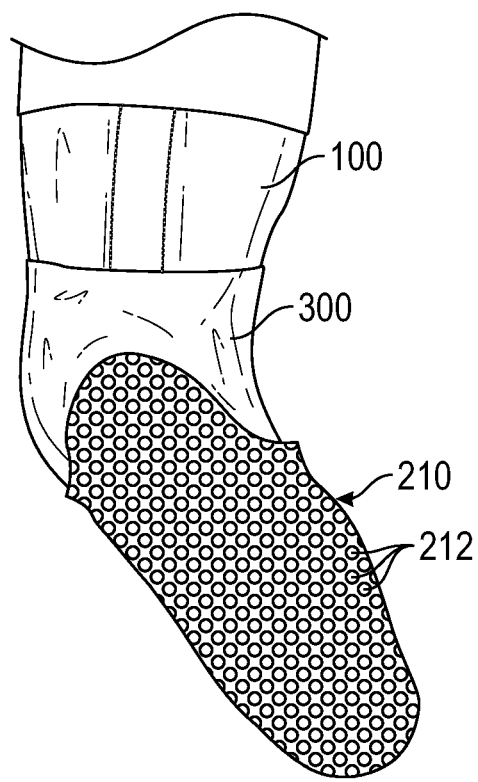
FIG. 8A illustrates a layer of a socket, according to an embodiment.

As illustrated in FIG. 8A, perforated inner layer 210 is an air-permeable layer that comprises a plurality of perforations or holes 212, through which air may pass. In an embodiment, each hole may be small (e.g., 5 millimeters or less in diameter) to avoid excessive tissue strain or other skin problems on the residual limb. Perforated inner layer 210 may be made from polypropylene, polyethylene, nylon, or other thermo-formable plastic, or a copolymer of such plastics.

Figure 8B:
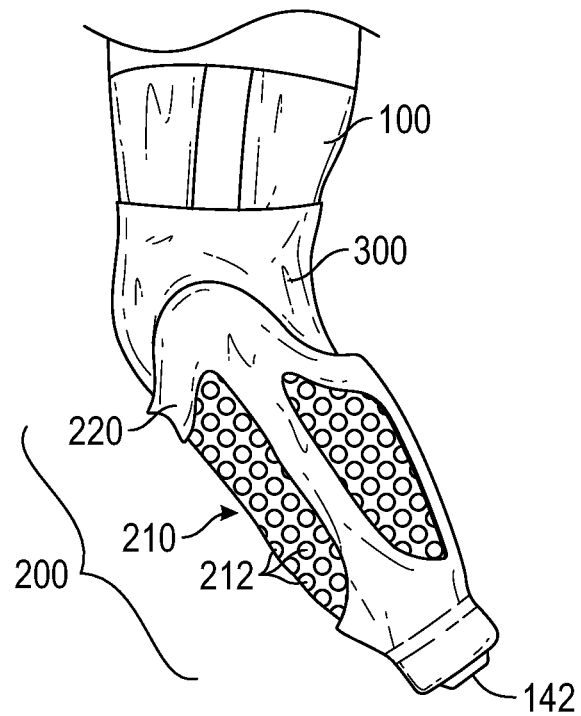
FIGS. 8B-8F illustrate various exterior views of a socket, according to a first embodiment.

As illustrated in FIG. 8B, outer frame 220 is attached over perforated inner layer 210. Outer frame 220 comprises one or more fenestrations or windows, which expose one or more portions of perforated inner layer 210 to the external environment. In the first embodiment, illustrated in FIGS. 8A-8F, outer frame 220 comprises three such fenestrations. Outer frame 220 may comprise or consist of carbon fiber for lightweight durability.

In an embodiment, socket 200 is custom made for the residual limb of its user. For example, perforated plastic may be drape-molded over a positive model of the user's residual limb or three-dimensionally printed, and covered in perforated, air-permeable fabric to create perforated inner layer 210. A carbon fiber outer frame 220 may then be molded over the custom-molded perforated inner layer 210, and the outer frame 220 may be affixed to the perforated inner layer 210 by standard means, such as stitching, adhesive, and/or the like. The perforations and fenestrations may be strategically positioned to provide breathability to the areas of the user's residual limb which heat up the most during the use of a prosthesis.

Figure 8C:
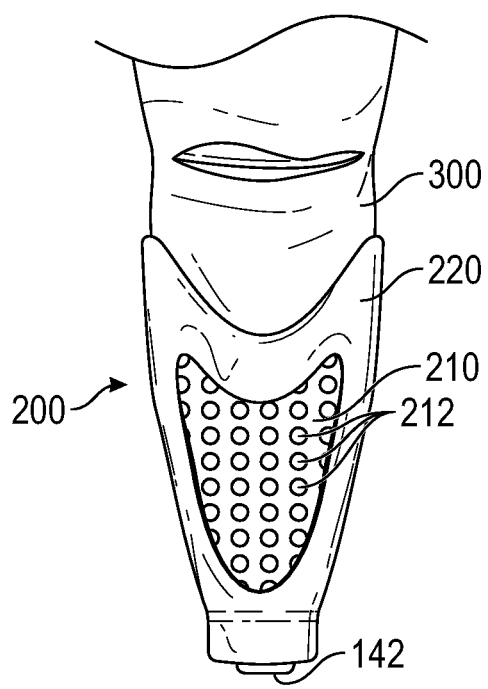
Figure 8D:
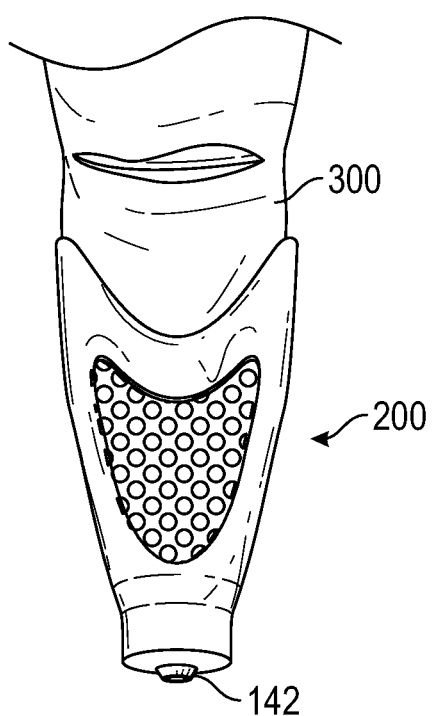

FIGS. 8C and 8D illustrate the front of socket 200 in plan view and perspective view, respectively. As illustrated, outer frame 220 comprises an anterior, symmetrical fenestration on the front of socket 200. This anterior fenestration enables air from the external environment to pass through perforated inner layer 210, via holes 212, to the internal environment of socket 200, and/or enables air from the internal environment of socket 200 to pass through perforated inner layer 210, via holes 212, to the external environment. The front of socket 200, illustrated in FIGS. 8C and 8D, corresponds to the anterior of the residual limb, and therefore, the anterior fenestration provides breathability, primarily, to the anterior of the user's residual limb.

Figure 8E:
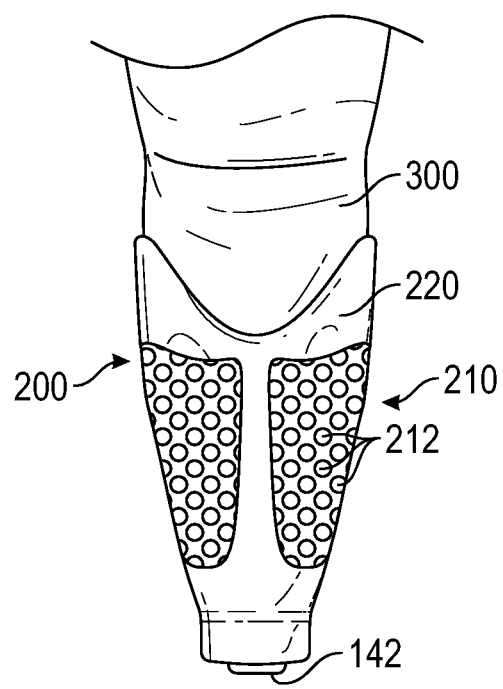
Figure 8F:
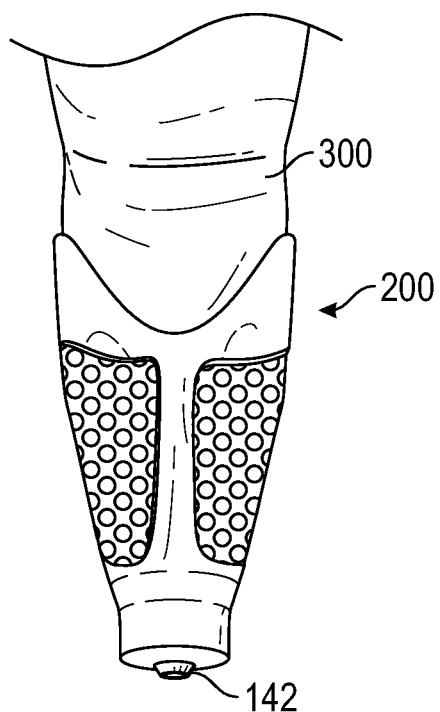

FIGS. 8E and 8F illustrate the back of socket 200 in plan view and perspective view, respectively. As illustrated, in the first embodiment, outer frame 200 comprises two, separate posterior fenestrations on the back of socket 200. Each posterior fenestration is offset from the center and separated from the other posterior fenestration by a strip of outer frame 220. Each posterior fenestration enables air from the external environment to pass through perforated inner layer 210, via holes 212, to the internal environment of socket 200, and/or enables air from the internal environment of socket 200 to pass through perforated inner layer 210, via holes 212, to the external environment. The back of socket 200 corresponds to the posterior of the residual limb, and therefore, the left-posterior fenestration provides breathability, primarily, to the left-posterior of the user's residual limb, while the right-posterior fenestration provides breathability, primarily, to the right-posterior of the user's residual limb. Advantageously, the posterior fenestrations allow air to reach the posterior of the user's residual limb, which is typically the area that heats up the most during use of prostheses.

Figure 9A:
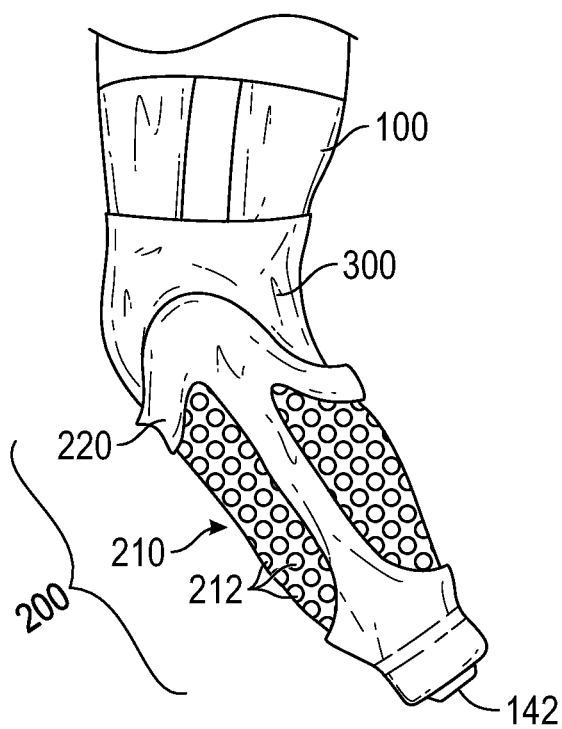
FIGS. 9A and 9B illustrate exterior views of a socket, according to a second embodiment.
Figure 9B:
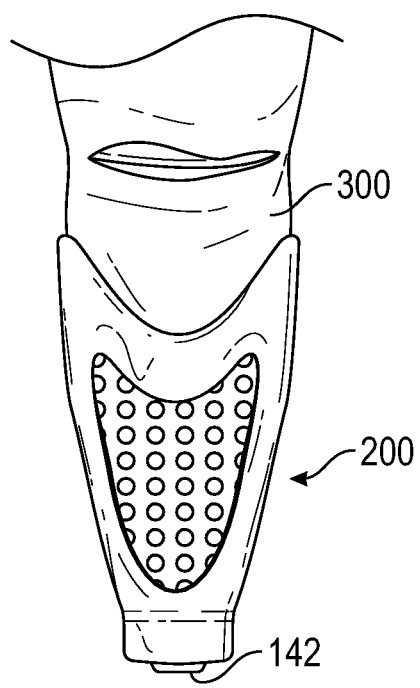

FIGS. 9A and 9B illustrate socket 200 in side and back plan views, respectively, according to a second embodiment. Unlike the first embodiment, the second embodiment only has a single posterior fenestration, which may be similar or identical to the anterior fenestration illustrated in FIGS. 8C and 8D. The second embodiment of socket 200 may have an anterior fenestration that is similar or identical to the anterior fenestration of the first embodiment of socket 200, illustrated in FIGS. 8C and 8D.

2. Usage of System

Figures 10A, 10B:
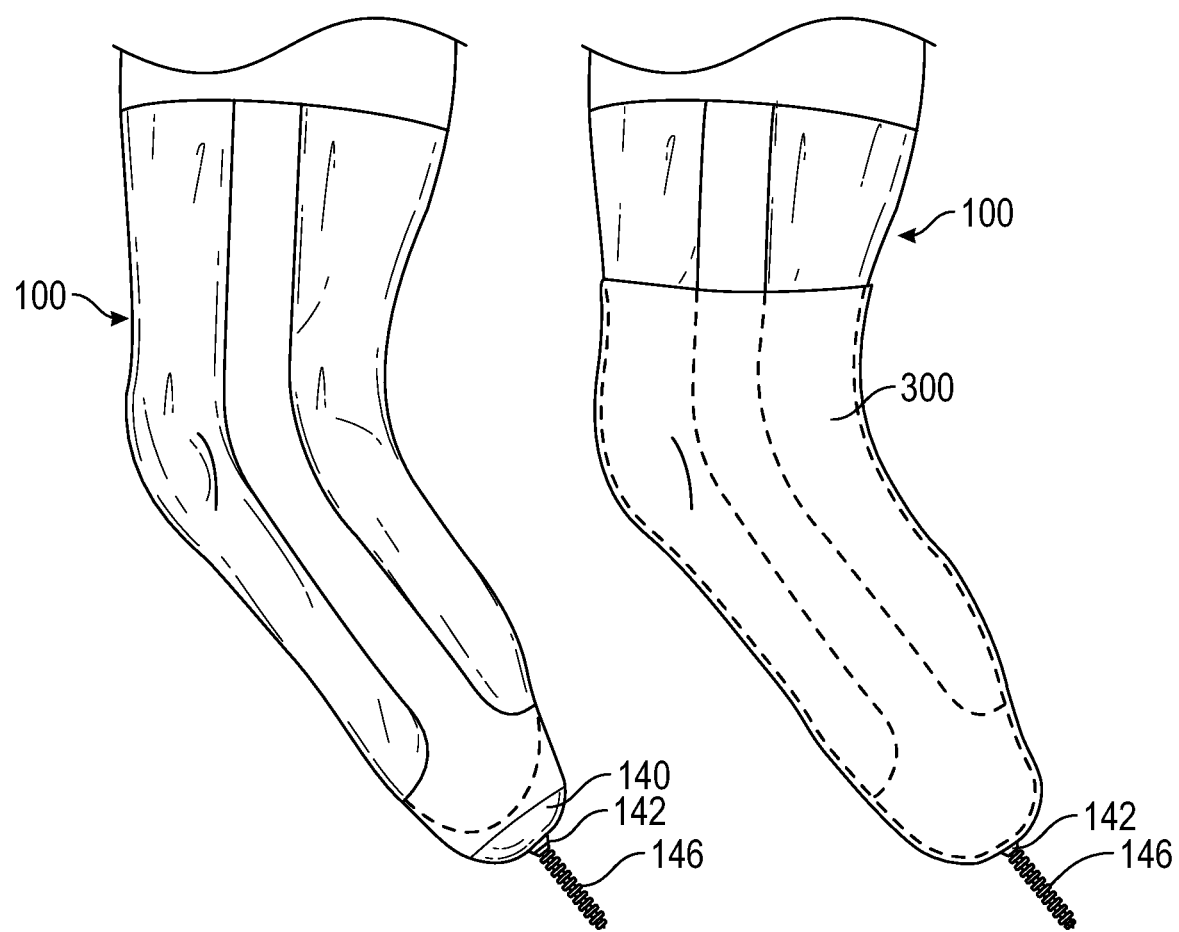
FIGS. 10A-10C illustrate usage of a liner sock and socket, according to an embodiment.
Figure 10C:
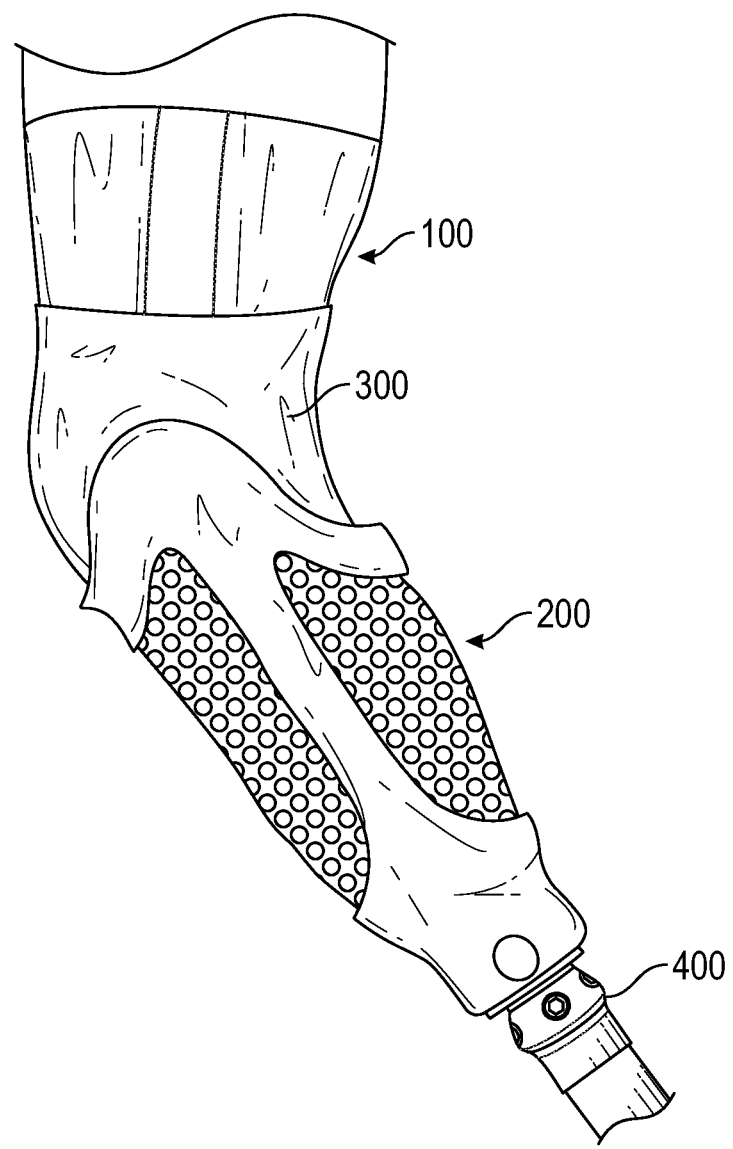

FIGS. 10A-10C illustrate how liner sock 100 and socket 200 may be used, according to an embodiment. As illustrated in FIG. 10A, liner sock 100 may be pulled over the residual limb. This may be performed by turning liner sock 100 inside-out (e.g., as illustrated in FIG. 1C), placing the distal end of the user's residual limb into distal cup 144, and then rolling liner sock 100 up onto the user's residual limb. It should be understood that liner sock 100 may be manufactured in a variety of sizes to fit a wide range of residual limbs. A pin screw 146 may be screwed into countersunk hole 142 on liner sock 100, either before or after stump sock 300 and/or socket 200 have been placed over liner sock 100.

As illustrated in FIG. 10B, stump sock 300 is pulled over liner sock 100. As described elsewhere herein, stump sock 300 provides volume management and may be replaced with a stump sock 300 of different ply, as needed over time, due to changes in the volume of the user's residual limb. In some cases, stump sock 300 may not be necessary, and may be omitted, in which case socket 200 may be placed directly over liner sock 100.

As illustrated in FIG. 10C, socket 200 is pulled over liner sock 100 and/or stump sock 300. Socket 200 may be held to liner sock 100 and the residual limb using a pin-suspension technique or other lanyard-style system on the sides or end of liner sock 100 (e.g., the system manufactured by Coyote Design™ of Boise, Idaho). In any case, a prosthesis (e.g., a prosthetic leg and foot) may be affixed to pin screw 146, with socket 200 providing suspension of the prosthesis from the residual limb. Any commercial pin-locking system may be used to affix the prosthesis to pin screw 146. While embodiments are illustrated herein as using pin suspension, it should be understood that these embodiments may be adapted to use other common suspension means, such as sleeve, suction, and/or elevated vacuum suspension.

Advantageously, as discussed above, liner sock 100 utilizes air-permeable textile(s), with internal strips 150, 152, and/or 153, or dots 156 of silicone gel or similar friction-interface material, to provide a comfort, friction fit. Because the outer surface of the air-permeable textile is uncovered and a significant amount of the inner surface of the air-permeable textile is uncovered, the textile of liner sock 100 admits air into the inner environment of liner sock 100 and allows sweat to evaporate from the surface of the user's residual limb. In other words, liner sock 100 improves breathability in the internal environment of liner sock 100.

Furthermore, as discussed above, socket 200 utilizes one or more fenestrations that expose a perforated inner layer 210 to the external environment. This allows air to pass between the internal and external environments of socket 200, via holes 212 in perforated inner layer 210. Therefore, socket 200 improves the breathability in the internal environment of socket 200.

Thus, the disclosed liner sock 100 and the disclosed socket 200, both individually and in combination, improve ventilation and breathability to the user's residual limb and provide an "air-conditioned" effect. It should be understood that, in the event that a stump sock 300 is used between liner sock 100 and socket 200, a stump sock 300 with breathable characteristics should be utilized, so as to not inhibit the improved breathability characteristics of the liner sock 100 and/or socket 200.

The above description of the disclosed embodiments is provided to enable any person skilled in the art to make or use the invention. Various modifications to these embodiments will be readily apparent to those skilled in the art, and the general principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. A system for use on a residual limb, the system comprising:
   a liner sock configured to be worn on and contact the residual limb, the liner sock comprising:
      air-permeable textile forming a substantially cylindrical portion that is closed on a distal end and open on a proximal end and comprising an internal surface and an external surface; and
      a friction-interface material that covers only a portion of the internal surface of the air-permeable textile, wherein the friction-interface material defines an inner surface of the liner sock such that, when worn on the residual limb, the friction-interface material directly contacts a surface of the residual limb, and an uncovered portion of the air-permeable textile which the friction-interface material does not cover allows air to pass between an external environment of the liner sock and the surface of the residual limb, wherein the friction-interface material comprises a plurality of strips that are spaced from each other to define the uncovered portion of the air-permeable textile therebetween,
      wherein the air permeable textile comprises:
         a first section comprising unidirectional-stretch textile; and
         at least one second section comprising bidirectional-stretch textile,
         wherein the first section is fixed to the at least one second section by at least one seam, and
         wherein the friction-interface material covers the at least one seam on the internal surface of the air-permeable textile.

2. The system of claim 1, wherein the air-permeable textile comprises two second sections comprising bidirectional-stretch textile.

3. The system of claim 1, wherein the friction-interface material covers an entire internal surface of the first section comprising unidirectional-stretch textile, but does not cover an entire internal surface of the at least one section comprising bidirectional-stretch textile.

4. The system of claim 1, wherein the friction-interface material comprises a plurality of longitudinal strips that extend in a longitudinal direction of the liner sock and that are spaced apart from each adjacent one of the plurality of longitudinal strips, around a circumference of the liner sock, by the uncovered portion of the air-permeable textile.

5. The system of claim 1, wherein the friction-interface material comprises a strip that extends around a circumference of the liner sock at a proximal end of the liner sock.

6. The system of claim 1, wherein the friction-interface material comprises a plurality of circumferential strips that extend around a circumference of the liner sock and that are spaced apart from each adjacent one of the plurality of circumferential strips, in a longitudinal direction of the liner sock, by the uncovered portion of the air-permeable textile.

7. The system of claim 1, wherein the friction-interface material comprises a distal cup at a distal end of the liner sock.

8. The system of claim 1, wherein the friction-interface material comprises silicone gel.

9. The system of claim 1, wherein the liner sock further comprises a distal cap on an external surface of the closed distal end of the liner sock.

10. The system of claim 9, wherein the distal cap comprises a countersunk threaded hole configured to receive a screw pin.

11. The system of claim 1, further comprising a socket to be worn, either directly or indirectly, over the liner sock, the socket comprising:
    a perforated inner layer; and
    an outer frame comprising one or more fenestrations, through which the perforated inner layer is exposed to an external environment of the socket.

12. The system of claim 11, wherein the perforated inner layer comprises a plurality of holes having a diameter of 5 millimeters or less.

13. The system of claim 11, wherein the outer frame comprises an anterior fenestration and at least one posterior fenestration.

14. The system of claim 13, wherein the outer frame comprises at least two posterior fenestrations.

15. The system of claim 11, wherein the perforated inner layer comprises fabric.

16. The system of claim 11, wherein the outer frame comprises carbon fiber.

17. The system of claim 1, wherein the at least one seam has a curvature, wherein the friction-interface material follows the curvature of the at least one seam.

18. The system of claim 1, wherein the liner sock has a longitudinal direction, wherein the unidirectional-stretch textile is oriented to elongate in the longitudinal direction.

* * * * *